(12) United States Patent
Kimura et al.

(10) Patent No.: US 6,252,230 B1
(45) Date of Patent: Jun. 26, 2001

(54) REFRACTION TYPE NON-DESTRUCTION MEASURING APPARATUS

(75) Inventors: Mikio Kimura; Akihiko Fujita, both of Ageo (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 0 days.

(21) Appl. No.: 09/181,933

(22) Filed: Oct. 28, 1998

(30) Foreign Application Priority Data

Oct. 29, 1997 (JP) .................................................. 9-297437

(51) Int. Cl.[7] .................................................. G01N 21/35
(52) U.S. Cl. .................................. 250/341.2; 250/339.07; 250/339.01
(58) Field of Search ........................... 250/341.2, 339.07, 250/399, 250/399.01

(56) References Cited

FOREIGN PATENT DOCUMENTS 62-91955 * 4/1987 (JP) .................................. 250/339.07
6-186159 * 7/1994 (JP) .................................. 250/339.07

* cited by examiner

Primary Examiner—Constantine Hannaher
Assistant Examiner—Andrew Israel
(74) Attorney, Agent, or Firm—Kubovcik & Kubovcik

(57) ABSTRACT

The refraction type non-destruction measuring apparatus of the present invention has a prism having a predetermined refractive index, projecting means for projecting near infrared light onto an object to be examined through the prism, a contact material filling the space between the object to be examined and the prism and having a refractive index set in conformity with the characteristic of the object to be examined, and light receiving means for receiving the internal reflected light of the light having entered the interior of the object to be examined through the contact material and the prism.

9 Claims, 5 Drawing Sheets

REFRACTION TYPE NON-DESTRUCTION MEASURING APPARATUS

BACKGROUND OF THE INVENTION

1. Field of the Invention

This invention relates to an apparatus for measuring the degree of sugariness of fruit or vegetables such as apples and peaches.

2. Related Background Art

As shown in FIG. 6 of the accompanying drawings, the juice of fruit or a vegetable has heretofore been used as an object 50 to be examined, and the object to be examined has been sandwiched between prisms 52 and 54 having the same refractive index.

In this apparatus, monochromatic visible light from a light source 56 enters the object 50 to be examined through the prisms 52 and 54, and the incident light is refracted by the difference between the refractive indices of the object 50 to be examined and the prisms 52, 54. A line sensor 58 for receiving the refracted light is divided into light and dark portions by the presence or absence of the application of emergent light.

The direction of emergence of the emergent light differs depending on the refractive index of the object to be examined and therefore, the refractive index of the object to be examined can be found from the boundary position of the refracted light which has arrived at the line sensor 58, and further, the degree of sugariness of the fruit or a vegetable which is the object to be examined is obtained (by the relational expression of ICUMSA (International Commission on Uniformity Method of Sugar Analysis) (Table 1).

TABLE 1

Relation between Brix and Refractive Index

| % | $n_D^{20}$ | % | $n_D^{20}$ | % | $n_D^{20}$ | % | $n_D^{20}$ | 1974 ICUMSA % | $n_D^{20}$ |
|---|---|---|---|---|---|---|---|---|---|
| 0 | 1.33299 | 20 | 1.36384 | 40 | 1.39986 | 60 | 1.44193 | 80 | 1.49071 |
| 1 | 1.33442 | 21 | 1.36551 | 41 | 1.40181 | 61 | 1.44420 | 81 | 1.49333 |
| 2 | 1.33586 | 22 | 1.36720 | 42 | 1.40378 | 62 | 1.44650 | 82 | 1.49597 |
| 3 | 1.33732 | 23 | 1.36889 | 43 | 1.40576 | 63 | 1.44881 | 83 | 1.49862 |
| 4 | 1.33879 | 24 | 1.37060 | 44 | 1.40776 | 64 | 1.45113 | 84 | 1.50129 |
| 5 | 1.34026 | 25 | 1.37233 | 45 | 1.40978 | 65 | 1.45348 | 85 | 1.50398 |
| 6 | 1.34175 | 26 | 1.37406 | 46 | 1.41181 | 66 | 1.45584 | 86 | 1.5067 |
| 7 | 1.34325 | 27 | 1.37582 | 47 | 1.41385 | 67 | 1.45822 | 87 | 1.5094 |
| 8 | 1.34477 | 28 | 1.37758 | 48 | 1.41592 | 68 | 1.46061 | 88 | 1.5121 |
| 9 | 1.34629 | 29 | 1.37936 | 49 | 1.41799 | 69 | 1.46303 | 89 | 1.5149 |
| 10 | 1.34782 | 30 | 1.38115 | 50 | 1.42009 | 70 | 1.46546 | 90 | 1.5177 |
| 11 | 1.34937 | 31 | 1.38296 | 51 | 1.42220 | 71 | 1.46790 | | |
| 12 | 1.35093 | 32 | 1.38478 | 52 | 1.42432 | 72 | 1.47037 | | |
| 13 | 1.35250 | 33 | 1.38661 | 53 | 1.42647 | 73 | 1.47285 | | |
| 14 | 1.35408 | 34 | 1.38846 | 54 | 1.42863 | 74 | 1.47535 | | |
| 15 | 1.35568 | 35 | 1.39032 | 55 | 1.43080 | 75 | 1.47787 | | |
| 16 | 1.35729 | 36 | 1.39220 | 56 | 1.43299 | 76 | 1.48040 | | |
| 17 | 1.35891 | 37 | 1.39409 | 57 | 1.43520 | 77 | 1.48295 | | |
| 18 | 1.36054 | 38 | 1.39600 | 58 | 1.43743 | 78 | 1.48552 | | |
| 19 | 1.36218 | 39 | 1.39792 | 59 | 1.43967 | 79 | 1.48811 | | |

In this example, monochromatic visible light is applied to an object 50 to be examined which is the juice of fruit or a vegetable through a prism 62. When the angle of incidence at this time is suitably selected, the incident light is totally reflected by the surface 64 of the object to be examined 50 which is in contact with the prism 62. A line sensor 58 which receives the totally reflected light is divided into light and dark portions by the presence or absence of the application of the reflected light. The angle at which the total reflection begins differs depending on the refractive index of the object to be examined and, therefore, it is similar to the above-described example of the prior art that the refractive index and the degree of sugariness of the fruit or vegetable which is the object to be examined are obtained from the boundary position of the line sensor 58.

In these apparatuses, however, juice had to be picked with the fruit or vegetable destroyed. Therefore, the fruit or vegetable had to be destroyed and consumed each time measurement was done, and the degree of sugariness of the fruit or vegetable to be sold could not be measured.

In contrast with these, an example of the prior art as shown in FIG. 8 of the accompanying drawings is known as a method of measuring an object to be examined without destroying it.

In this example, fruit or a vegetable which is not yet destroyed is used as an object 66 to be examined, instead of the object 50 to be examined in FIG. 7. The principle of measurement is similar to that in the example of FIG. 7.

However, if the contact between the prism 62 and the surface 68 of the object to be examined is insufficient or if air is present near it, total reflection does not take place on the surface 68 of the object to be examined. Also, if the surface of the object to be examined has an inclination angle with respect to the prism 62, accurate measurement cannot be done due to the influence of this inclination angle.

Further, an apparatus using near infrared absorption analysis has been put into practical use as a method of measuring fruit or a vegetable without destroying it, but this apparatus is bulky and expensive, and requires a power source.

SUMMARY OF THE INVENTION

To solve the above-noted problems, the present invention provides a refraction type non-destruction measuring apparatus having a prism having a predetermined refractive index, projecting means for projecting near infrared light onto an object to be examined through the prism, a contact material filling the space between the object to be examined and the prism and having a refractive index set in conformity with the characteristic of the object to be examined, and light receiving means for receiving the interval reflected light of the light having entered the interior of the object to be examined through the contact material and the prism.

DESCRIPTION OF THE PREFERRED EMBODIMENTS

Figure 1:
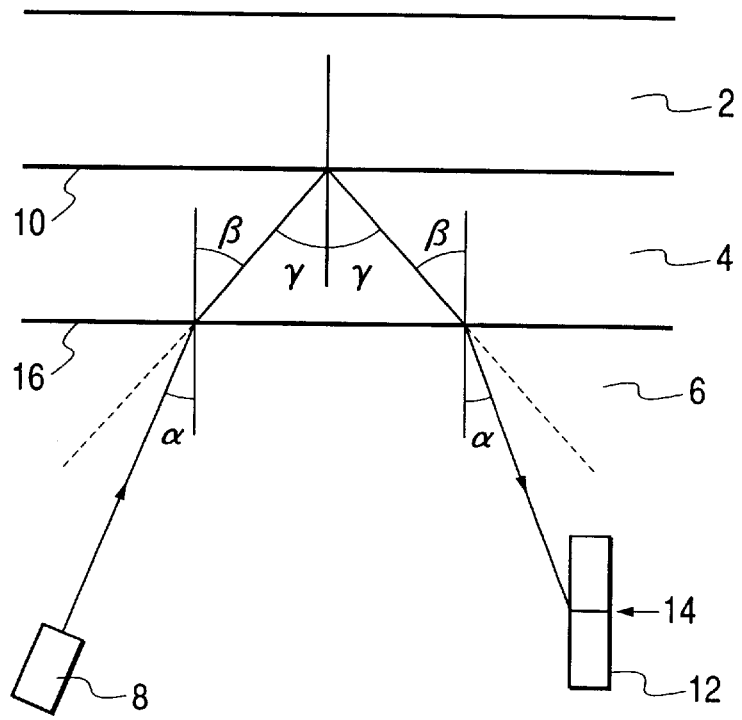
FIG. 1 shows a first embodiment of the present invention.

FIG. 1 shows a first embodiment of the present invention.

An object 2 to be examined is in contact with a prism 6 through a contact material 4. Light projected from a light source 8 is applied to the object 2 to be examined through the prism 6 and the contact material 4. The reflected light of this light from the surface 10 of the object to be examined emerges through the contact material 4 and the prism 6 and is detected by a line sensor 12.

The object 2 to be examined is fruit or a vegetable such as an apple or a peach. The light projected from the light source 8 onto the object 2 to be examined is near infrared light having good transmittability to fruit or vegetables, and monochromatic light having its center wavelength at 700 to 720 nm or 790 to 810 nm is used as this light. Such projected light is used and therefore, the projected 5 light is not intercepted by the surface 10 of the object to be examined, and can be projected onto the interior of the object 2 to be examined without destroying the object to be examined.

The gel of transparent silicon having elasticity is used as the contact material 4. By using such a contact material, it becomes possible to bring it into contact with the prism 6 without interposing air on the way to the prism even if the surface 10 of the object to be examined is not flat.

Also, the refractive indices Np, Nc and Ns of the prism 6, the contact material 4 and the object 2 to be examined, respectively, are made to have the following relation:

$$Np > Nc > Ns \qquad (1)$$

The present invention intends to measure the critical angle when the light projected from the light source 8 onto the object 2 to be examined is totally reflected by the surface 10 of the object to be examined by the line sensor 12, and to measure the refractive index of the object to be examined and further the degree of sugariness of the fruit or vegetable which is the object to be examined from the critical angle. That is, when expression (1) is established, the light projected from the light source 8 at an angle of incidence a is refracted at an angle $\beta$ smaller than $\alpha$, from the relation that Np>Nc. At this time, $$Np \cdot \sin \alpha = Nc \cdot \sin \beta.$$

(Snell's law). When this refracted light is incident on the surface 10 of the object to be examined at an angle exceeding a certain critical angle $\gamma$ due to the relation that Nc>Ns, total reflection takes place. At angles smaller than $\gamma$, there coexist the refracted light and reflected light to the interior of the object to be examined. From expression (1), it never happens that total reflection takes place on the boundary surface between the contact material 4 and the prism 6 before total reflection takes place on the surface of the object 2 to be examined beyond the critical angle $\gamma$. The light reflected from the object 2 to be examined is refracted again in the boundary between the contact material 4 and the prism 6 and arrives at the line sensor 12.

In the line sensor 12 the difference between light and darkness appears on the portion thereof irradiated with the reflected light by the total reflection from the object 2 to be examined and the portion thereof not irradiated. The critical angle $\gamma$ on the surface 10 of the object 2 to be examined can be found from the critical value 14 of the light and darkness, the refractive index Np of the prism 6, the refractive index Nc of the contact material 4 and the angle $\alpha$. Thereby the refractive index of the object 2 to be examined can be found. The degree of sugariness of the fruit or vegetable which is the object to be examined can be found from the refractive index thereof by the relational expression of ICUMSA (International Commission on Uniformity Method of Sugar Analysis) (Table 1).

Figure 2:
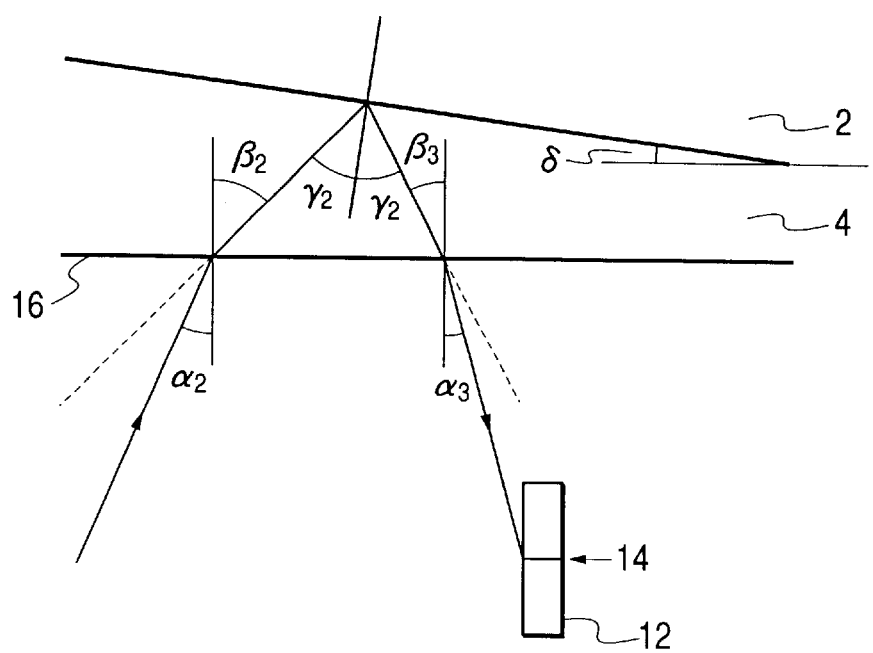
FIG. 2 shows a second embodiment of the present invention.

FIG. 2 shows a second embodiment of the present invention in which the surface of the object to be examined is slightly inclined with respect to the surface of a prism 16. The inclination angle is $\delta$. In such a case, the boundary value 14 on a line sensor 12 created by light totally reflected on the surface 10 of the object to be examined is fluctuated by the inclination. In the present embodiment, the relations among the constructions and refractive indices of the object to be examined, the contact material and the prism are similar to those in the first embodiment, but the refractive indices of the object to be examined and the contact material are very approximate values (or may be the same value).

$$Np > Nc \geq Ns$$

At this time, the following relations exist:

$$Np \cdot \sin \alpha_2 = Nc \cdot \sin \beta_2$$

$$Nc \cdot \sin \gamma_2 = Ns$$

$$Nc \cdot \sin \beta_3 = Np \cdot \sin \alpha_3$$

$$\beta_2 = \gamma_2 + \delta$$

$$\beta_3 = \gamma_2 - \delta$$

Further, by $\delta$ being minute, $$\cos \delta = 1$$

$$\sin \delta = \delta.$$

From the above-mentioned relations, $$\sin \alpha_2 = \frac{Ns}{Np} - \frac{Nc}{Np} \delta \sqrt{1 - \left(\frac{Ns}{Nc}\right)^3} \qquad (2)$$

and the angle of total relation $\alpha_3$ depends on the refractive index Nc and the inclination angle $\delta$ of the contact material.

Figure 3:
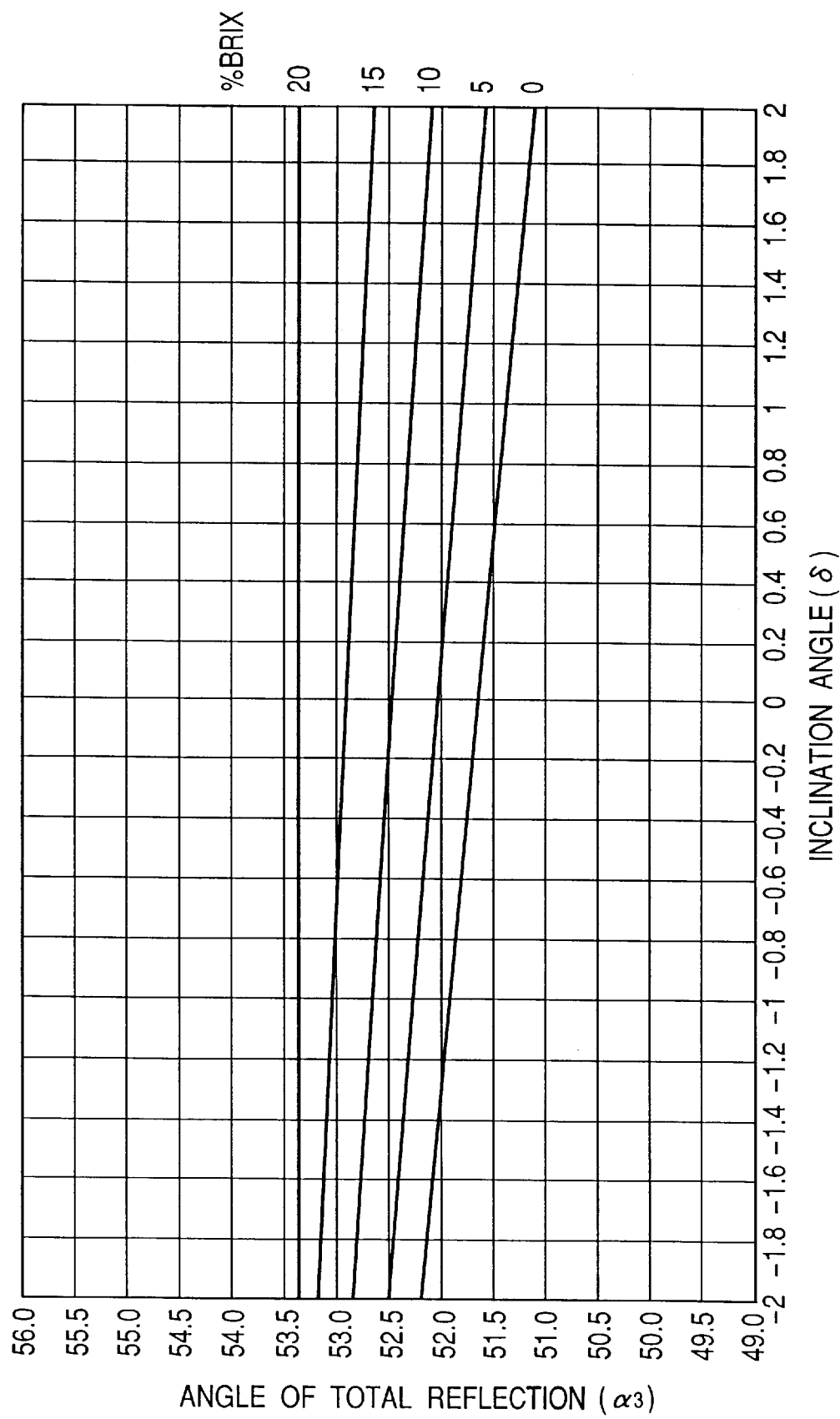
FIG. 3 is a graph showing the relation between an inclination angle and the angle of total reflection.

In the present embodiment, the refractive index Nc of the contact material and the refractive index Ns of the object to be examined are approximate values or the same value and therefore, it is seen from expression (2) that the angle of total reflection $\alpha_3$ assumes a value having no relation with the inclination angle. This is shown in FIG. 3. FIG. 3 represents changes in the angle of total reflection $\alpha_3$ relative to the inclination angle $\delta$ when in expression (2), Ns=1.3329 to 1.36384 (0 to 20% Brix) and Nc=1.36384 (20% Brix) and Np=1.7 and Ns=0, 5, 10, 15, 20% Brix. As can be seen from this graph, if the refractive index Nc of the contact material and the refractive index Ns of the object to be examined are the same value, namely, Nc=Ns=1.36384 (20% Brix), the angle of total reflection $\alpha_3$ assumes a constant value having no relation with the inclination angle $\delta$. It is also seen that the more approximate values Nc and Ns assume, the smaller becomes the influence of the inclination angle upon the angle of total reflection. The other action and effect of the present embodiment are similar to those of the first embodiment.

Figure 4:
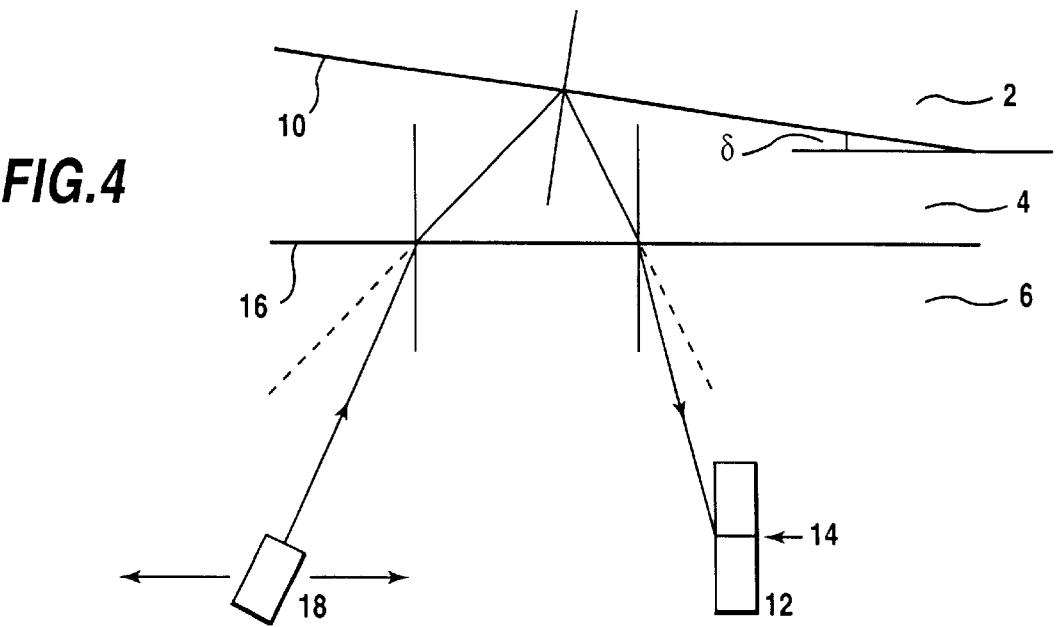
FIG. 4 shows a third embodiment of the present invention.

FIG. 4 shows a third embodiment of the present invention.

The third embodiment has a light source 18 movable in parallelism to the prism surface 16 of the prism 6. The constructions of the prism 6, the contact material 4, the object 2 to be examined and the line sensor 12 are similar to those in the first embodiment and the second embodiment. The relations among the refractive indices Np, Nc and Ns of the prism 6, the contact material 4 and the object 2 to be examined, as in the first embodiment, are $$Np > Nc > Ns.$$

Since the light source 18 is movable in parallelism to the prism surface 16, the angle of incidence on the prism surface 16 is always constant.

The surface 10 of the object 2 to be examined has an inclination with respect to the prism surface 16, and the boundary value 14 on the line sensor created by the light totally reflected on the surface 10 of the object to be examined is fluctuated by the inclination. However, by the construction of the present embodiment, the light source 18 is moved and projects light, and lights totally reflected by several locations on the surface 10 of the object to be examined which correspond to the movement of the light source 18 are detected as a plurality of boundary values 14 on the line sensor 12. It is possible to eliminate the influence of the inclination angle 6 by averaging these boundary values. If as in the second embodiment, $$Np > Nc \geq Ns,$$

it will be possible to measure the refractive index of the object to be examined more accurately.

Figure 5A:
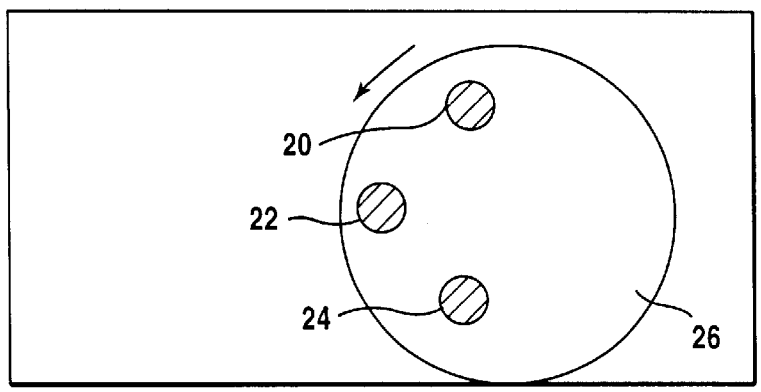
FIGS. 5A and 5B are a top plan view and a cross-sectional view, respectively, showing a fourth embodiment of the present invention.
Figure 5B:
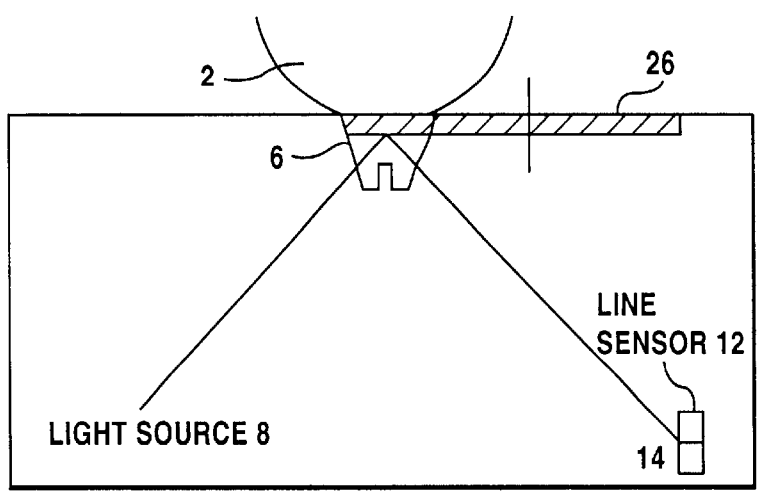
Figure 6:
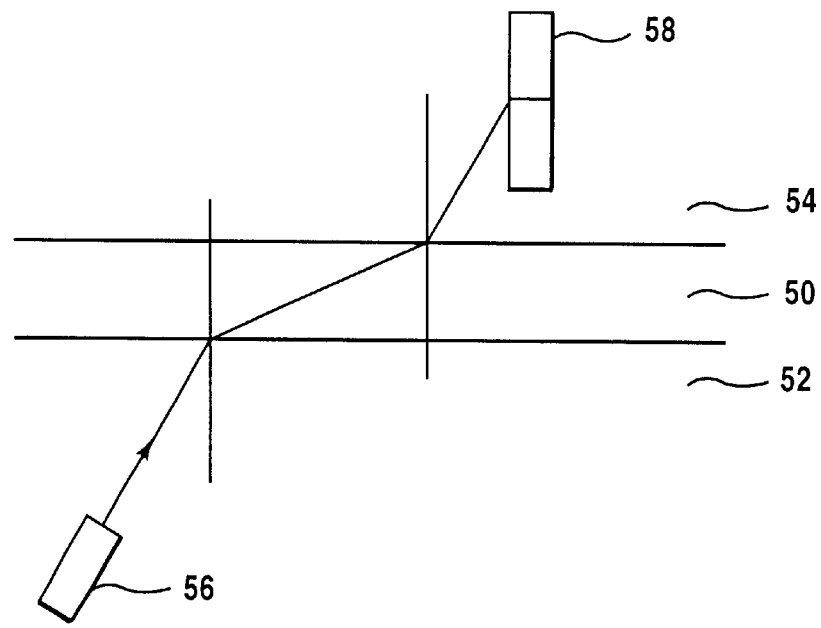
FIG. 6 shows an example of the prior art.
Figure 7:
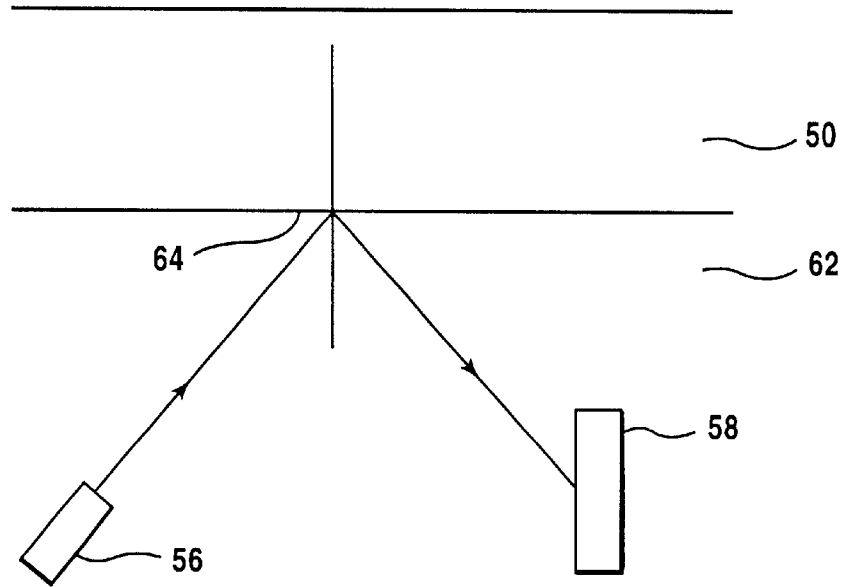
FIG. 7 shows an example of the prior art.
Figure 8:
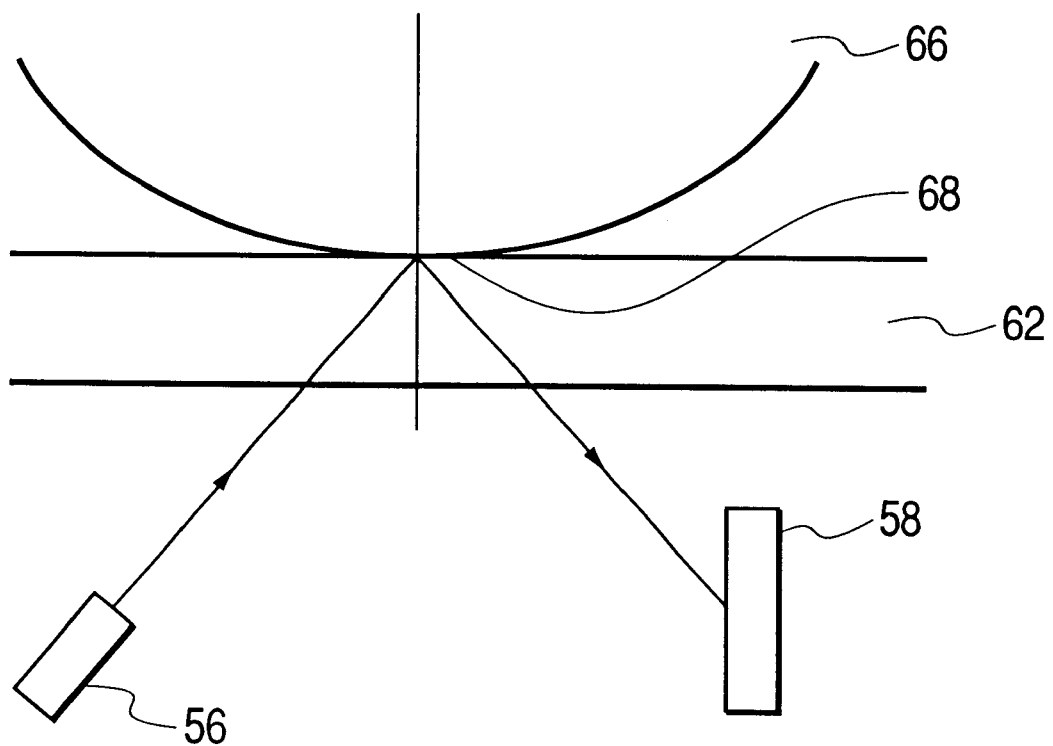
FIG. 8 shows an example of the prior art.

FIGS. 5A and 5B show a fourth embodiment of the present invention. In this embodiment, three kinds of contact materials 20, 22 and 24 are disposed in a rotating mechanism 26. By the rotation of the rotating mechanism 26, it is possible to select a contact material to be used and dispose it on the prism 6. The object 2 to be examined may be placed on the contact material before or after the selection of the contact material. The contact between the prism 6 and the selected contact material and between the contact material and the object 2 to be examined is sufficient owing to the gravity of the object 2 to be examined and the elasticity of the contact material, and it does not happen that air intervenes between the prism 6 and the contact material or between the contact material and the object 2 to be examined. The three kinds of contact materials have different refractive indices.

In the present embodiment, the light projected from the light source 8 is applied to the object 2 to be examined through the prism 6 and the selected contact material, and the light reflected by the surface 10 of the object to be examined emerges through the contact material and the prism 6, and is detected by the line sensor 12.

When the object 2 to be examined is inclined with respect to the prism surface 16, the boundary value 14 on the line sensor created by the light totally reflected on the surface 10 of the object to be examined is fluctuated by the inclination. In the construction of the present embodiment, however, the contact materials of different refractive indices are usable and therefore, by selecting a contact material having a refractive index most approximate to the refractive index of the object to be examined, it is possible to suppress the influence of the inclination of the object 2 to be examined as shown in FIG. 3.

Any number of contact materials more than two may be adopted, and the greater is the number, the more accurate measurement can be effected.

In the first to fourth embodiments, the contact material may be a high refractive index solution such as cane sugar contained in a transparent bag having strength, or a high refractive index solution itself such as cane sugar.

Also, the object to be examined may be liquid flowing through a pipe in a factory. In this case, measurement is effected with the space between the window of the pipe and the prism filled with the contact material. Further, the object to be examined may be liquid in a container of glass or the like. In this case, measurement is effected with the space between the surface of the container and the prism filled with the contact material.

As described above, according to the present invention, the degree of sugariness of fruit or vegetables can be measured irrespective of the shape of the fruit or vegetables without the fruit or vegetables being destroyed.

Further, no power source is necessary and the apparatus can be made compact and portable and is easy and inexpensive to manufacture.

What is claimed is:

1. A refraction type non-destruction measuring apparatus for measuring a refractive index of an interior of an object to be examined by non-destruction comprising:

a prism having a predetermined refractive index;

projecting means for projecting near infrared light onto said object to be examined through said prism;

a contact material filling space between said object to be examined and said prism, and having a refractive index set in conformity with the characteristic of said object to be examined; and light receiving means for receiving an internal reflected light of a light having entered the interior of said object to be examined through said contact material and said prism;

wherein a refractive index Np of said prism, a refractive index Nc of said contact material and a refractive index Ns of said object to be examined have the relation Np>Nc>Ns.

2. A refraction type non-destruction measuring apparatus according to claim 1, wherein said object to be examined is fruit or vegetable, and the degree of sugariness of said fruit or vegetable is measured by the refractive index thereof.

3. A refraction type non-destruction measuring apparatus according to claim 1, wherein said contact material is an elastic substance like a gel of transparent silicon.

4. A refraction type non-destruction measuring apparatus according to claim 1, wherein said projecting means is movable in parallel with one of the surface of said prism which is in contact with said contact material or said object to be examined.

5. A refraction type non-destruction measuring method of measuring a refractive index Ns of an interior of an object to be examined by non-destruction comprising the steps of:

filling space between said object to be examined and a prism having a predetermined refractive index Np with a contact material comprising a refractive index Nc set in conformity with characteristic of said object to be examined;

projecting near infrared light onto said object to be examined through said prism; and receiving an internal reflected light of the light having entered the interior of said object to be examined through said contact material and said prism;

wherein Np>Nc>Ns.

6. A refraction type non-destruction measuring apparatus for measuring a refractive index of an interior of an object to be examined by non-destruction comprising:

a prism having a predetermined refractive index;

projecting means for projecting near infrared light onto said object to be examined through said prism;

a contact material filling space between said object to be examined and said prism, and having a refractive index set in conformity with the characteristic of said object to be examined; and light receiving means for receiving an internal reflected light of a light having entered the interior of said object to be examined through said contact material and said prism;

wherein said object to be examined is liquid passing through a pipe.

7. A refraction type non-destruction measuring apparatus for measuring a refractive index of an interior of an object to be examined by non-destruction comprising:

a prism having a predetermined refractive index;

projecting means for projecting near infrared light onto said object to be examined through said prism;

a contact material filling space between said object to be examined and said prism, and having a refractive index set in conformity with the characteristic of said object to be examined; and light receiving means for receiving an internal reflected light of a light having entered the interior of said object to be examined through said contact material and said prism;

wherein said contact material is a high refractive index solution such as cane sugar contained in a transparent bag having strength.

8. A refraction type non-destruction measuring apparatus for measuring a refractive index of an interior of an object to be examined by non-destruction comprising:

a prism having a predetermined refractive index;

projecting means for projecting near infrared light onto said object to be examined through said prism;

a contact material filling space between said object to be examined and said prism, and having a refractive index set in conformity with the characteristic of said object to be examined; and light receiving means for receiving an internal reflected light of a light having entered the interior of said object to be examined through said contact material and said prism;

wherein said contact material is a high refractive index solution such as cane sugar.

9. A refraction type non-destruction measuring apparatus for measuring a refractive index of an interior of an object to be examined by non-destruction comprising:

a prism having a predetermined refractive index;

projecting means for projecting near infrared light onto said object to be examined through said prism;

a contact material filling space between said object to be examined and said prism, and having a refractive index set in conformity with the characteristic of said object to be examined; and light receiving means for receiving an internal reflected light of a light having entered the interior of said object to be examined through said contact material and said prism;

wherein said contact material is provided in a plurality, and one of said plurality of contact materials is selectively insertable between said object to be examined and said prism.

* * * * *